(12) United States Patent
Takamori et al.

(10) Patent No.: US 8,152,524 B2
(45) Date of Patent: Apr. 10, 2012

(54) DENTAL HANDPIECE

(75) Inventors: Shoichi Takamori, Kanuma (JP); Yusuke Harikae, Kanuma (JP)

(73) Assignee: Nakanishi Inc., Kanuma-Shi, Tochigi (JP)

( * ) Notice: Subject to any disclaimer, the term of this patent is extended or adjusted under 35 U.S.C. 154(b) by 219 days.

(21) Appl. No.: 12/207,933

(22) Filed: Sep. 10, 2008

(65) Prior Publication Data
US 2009/0246730 A1 Oct. 1, 2009

(30) Foreign Application Priority Data
Sep. 13, 2007 (JP) .................................. 2007-237421

(51) Int. Cl.
*A61C 3/02* (2006.01)

(52) U.S. Cl. ........................................................ 433/88
(58) Field of Classification Search ...................... 433/88
See application file for complete search history.

(56) References Cited

U.S. PATENT DOCUMENTS

| 5,857,851 | A * | 1/1999 | Chavanne ........................ 433/88 |
| 2001/0031441 | A1* | 10/2001 | Ito et al. ........................... 433/88 |
| 2003/0180684 | A1 | 9/2003 | Sierro et al. |

FOREIGN PATENT DOCUMENTS

| EP | 1 145 689 A2 | 10/2001 |
| EP | 1 346 700 A1 | 9/2003 |
| WO | 02/26156 A1 | 4/2002 |

OTHER PUBLICATIONS

International Search Report.

* cited by examiner

*Primary Examiner* — John J Wilson
(74) *Attorney, Agent, or Firm* — Pearne & Gordon LLP

(57) ABSTRACT

Two nozzles 37 in pair are provided along an inner circumferential surface 21a of a concavity 21, air is blown out in a space from a blowout hole 37a provided at a tip end portion of the nozzle from a side where the nozzle 37 is provided aiming at an opposite side along an inner circumferential surface of the space and a powder contained in the concavity 21 is caused to rise up in the space, whereby the condition of the powder mixed with the air within the space is improved.

6 Claims, 8 Drawing Sheets

DENTAL HANDPIECE

BACKGROUND OF THE INVENTION

1. Field of the Invention

The present invention relates to a dental handpiece used in performing dental care by blowing a mixture of a powder and air on teeth along with water.

2. Description of the Related Art

There is known a dental handpiece used in blowing a mixture of a powder and air on the surfaces of teeth along with water, the powder being obtained by mixing a powder for polishing or cleaning teeth with air.

Such a dental handpiece is provided, for example, with a vessel for housing a powder, an air supply path for supplying air to the interior of the vessel, a mixture conveyance path for conveying a mixture of a powder and air to a jet nozzle, and a water conveyance path for conveying the water to be blown on the surfaces of teeth along with the mixture to a jet nozzle. In this dental handpiece, a pipe in communication with the air supply path and a pipe in communication with the mixture conveyance path are each provided in a protruding manner within the vessel, and a hole is drilled in the tip end of each of the protruding pipes so as to provide an air blowout hole and a mixture suction hole.

In a dental handpiece of this kind, it is required that a powder be mixed with air at an appropriate concentration and, therefore, there have been also proposed dental handpieces in which protruding pipes of an air blowout hole and of a mixture suction hole are arranged so that the air blowout hole and the mixture suction hole are positioned roughly in a middle region of a vessel (refer to Japanese Patent No. 3493129, for example). However, a handpiece is grasped in various positions when a dentist is performing care and, therefore, the concentration of a mixture of a powder and air in the vessel is not always appropriate. Furthermore, when a handpiece is held in such a position that the air blowout hole is buried under the powder and air supply to the interior of the vessel is stopped, the powder flows backward from the air blowout hole to the air supply path, posing problems such as the clogging of the air supply path and a decrease in the supply volume of the air.

Therefore, to solve problems as described above and thereby to provide a dental handpiece capable of obtaining an appropriate concentration of a mixture by the mixing of a powder and air within the vessel and capable of preventing the backflow of the powder to the air supply path regardless of the position of the handpiece, the applicant of the present invention has already made a proposal (refer to Japanese Patent No. 3299736, for example).

The technique based on this proposal is as follows. That is, the inside of the vessel for housing a powder therein is formed with curved surfaces so that air can swirl in all directions inside, the air supply path for supplying air to the interior of the vessel and mixing the powder and the air is divided into a plurality of branch pipes within the vessel, the branch pipes are extended to the vicinity of the curved surfaces inside the vessel in the middle region of the vessel, and a plurality of holes, which are aimed to cause the air to flow along the curved surface, are provided at the tip end of the branch pipe.

However, when a detailed examination was later made into conventional products to which the technique proposed by the applicant of the present invention was applied, it became apparent that there is room for improvement in the amount of a blown-out powder and the cutting efficiency.

That is, in conventional products, when a powder, air and water are blown, with the powder contained within the vessel to a predetermined upper limit level, it became apparent that the amount of the blown-out powder is large in the initial stage after the start of the blowout and that the amount of the blown-out powder decreases when the amount of the powder in the vessel decreases. This tendency in a change in the flow rate provides the advantage that the effect of cleaning can be easily visually ascertained in the initial stage after the start of the cleaning of the surfaces of teeth, but poses the problem that the powder filled in the vessel is used up in a short time.

Furthermore, it is requited that the cutting efficiency occurring in cleaning the surfaces of teeth by blowing a powder, air and water be constantly improved. Although the cutting efficiency may be improved simply by increasing the flow rate of the powder, the tendency that the powder in the vessel is used up in a short time is made more remarkable thereby.

The present invention has been made on the basis of such a technical problem and has as its object the provision of a dental handpiece that stabilizes the flow rate of a blown-out powder while raising the cutting efficiency and enables the stock of the powder filled in the vessel to last longer.

SUMMARY OF THE INVENTION

In consideration of the above-described object, the present invention provides a dental handpiece used to perform dental care by blowing a mixture of air and a powder on teeth along with water from a jet nozzle, which comprises: a vessel having a spherical space that contains the powder therein; an air supply path that supplies the air to be mixed with the powder to the space; a mixture conveyance path for conveying the mixture of the powder and the air to the jet nozzle by sucking the mixture roughly from a middle part of the space; and a water conveyance path for conveying water to be blown on teeth along with the mixture to the jet nozzle. The air supply path is provided with blowout means that blows out the air into the space within the vessel in the vicinity of a wall surface of the vessel, and the blowout means has, within the vessel, two blowout holes in pair that blow out the air from a side where the blowout means is provided aiming at an opposite side thereof along the wall surface of the vessel. When the air is blown out from the side of one end of the space where the blowout means is provided along the wall surface of the vessel, due to the Coanda effect the air flows from the side of one end of the space to the side of the other end along the wall surface of the vessel. As a result of this, a swirl is generated in the spherical space, thereby making it possible to improve the mixed condition of the powder and the air.

The blowout means may have any construction so long as the blowout means can blow out the air in the space from a side where the blowout means is provided aiming at an opposite side thereof along the wall surface of the vessel. However, for example, it is preferred that the blowout hole be formed so as to blow out the air aiming at a part where the width of the space becomes a maximum as viewed from the blowout means.

The blowout means can also be constructed in such a manner that there is formed another blowout hole that blows out the air aiming at the vicinity of a top surface level of the powder within the space. As a result of this, when the amount of the contained powder is large, the air blown out of this blowout hole can cause the powder in the vicinity of the surface of the powder that has accumulated within the space to rise up.

Furthermore, the blowout means can also be constructed in such a manner that there is formed another blowout hole that blows out the air aiming at a bottom part of the space. As a result of this, when the amount of the powder contained in the space is small, it is possible to cause the powder to rise up from the bottom part of the space.

It is preferred that the blowout means be provided with positioning means for positioning the mounting angle to the vessel. As a result of this, it is possible to position the vessel at an appropriate angle and in an appropriate position.

Incidentally, the water conveyance path can also be formed by burying a pipe in the interior of the vessel. The water conveyance path can also be formed by providing a pipe along an external surface of the vessel.

According to the present invention, in the blowout means that blows out air into a space where a powder and the air are to be mixed, a stream of air is generated along an inner circumferential surface of the space by the air that has been blown out into the space from first blowout holes formed at a tip end of the blowout means. As a result of this, within the space the powder contained is caused to rise up, thereby making it possible to improve the mixed condition of the powder and the air in the space.

Furthermore, when the amount of the contained powder is large, the air blown out of the second blowout hole formed in an outer circumferential surface of the blowout means causes the powder in the vicinity of the surface belonging to the powder accumulated within the space to rise up, thereby making it possible to improve the mixed condition of the powder and the air in the space.

On the other hand, when the remaining amount of the powder is small, the air that has been blown out of a third blowhole formed in the outer circumferential surface of the blowout means can cause the powder to rise up from a bottom part of the vessel, and also in this condition, it is possible to improve the mixed condition of the powder and the air in the space.

As described above, the mixed condition of the powder and the air in the space is improved and in addition, the mixing of the powder and the air can be promoted when the amount of the powder is large as well as when amount of the powder is small. Therefore, it is possible to stabilize the flow rate of a blown-out powder and it is possible to enable the stock of the filled powder to last longer while raising the cutting efficiency.

BRIEF DESCRIPTION OF THE DRAWINGS

FIG. 4A being a perspective view, FIG. 4B being a diagram as viewed from a direction orthogonal to an axis line of the blowout nozzle body, FIG. 4C being a side view of FIG. 4B, and FIG. 4D being a sectional view of a nozzle;

DETAILED DESCRIPTION OF THE PREFERRED EMBODIMENTS

The present invention will be described in detail below on the basis of an exemplary embodiment shown in the accompanying drawings.

Figure 1:
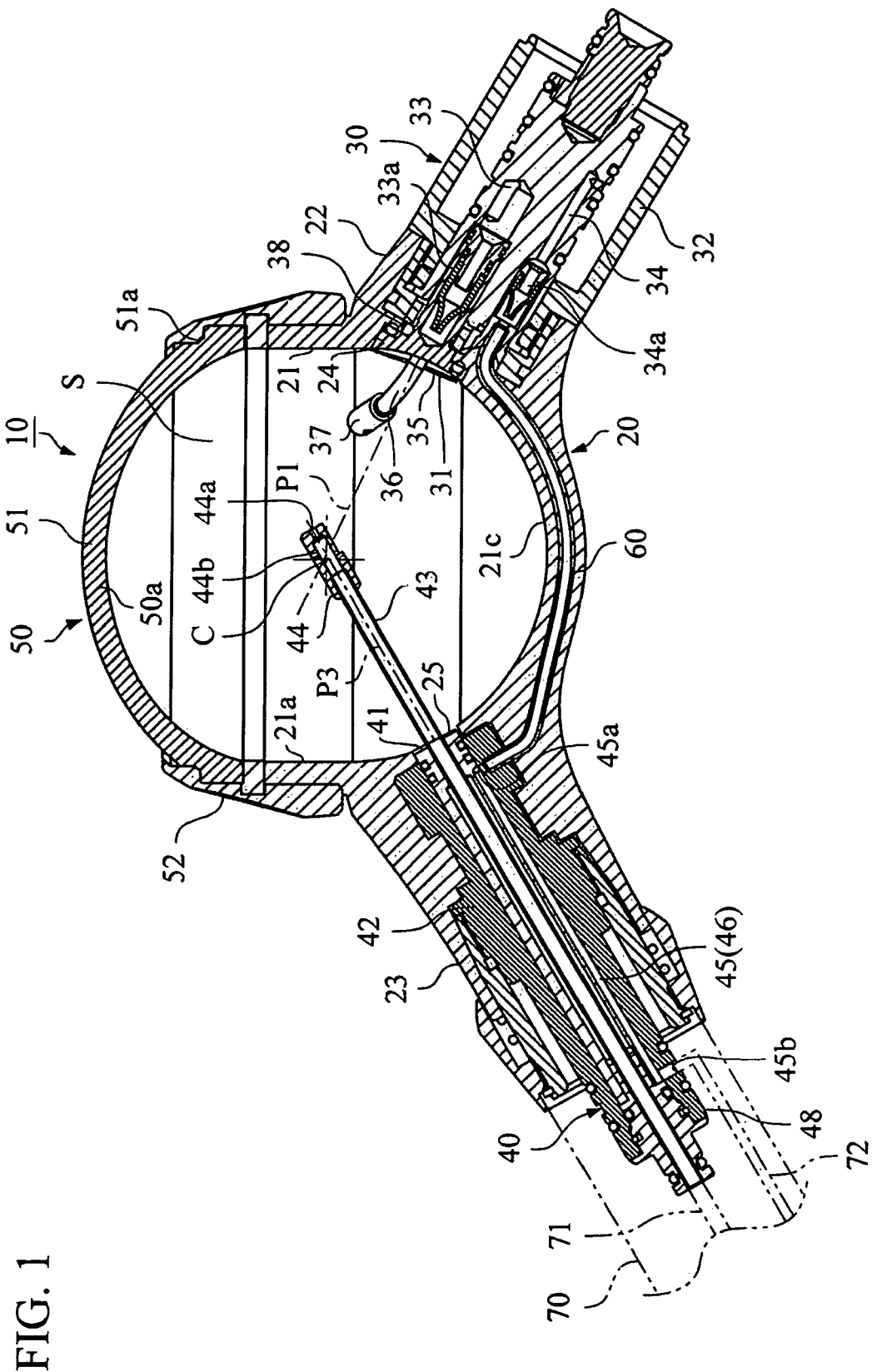
FIG. 1 is a sectional view of a handpiece in this exemplary embodiment.
Figure 2:
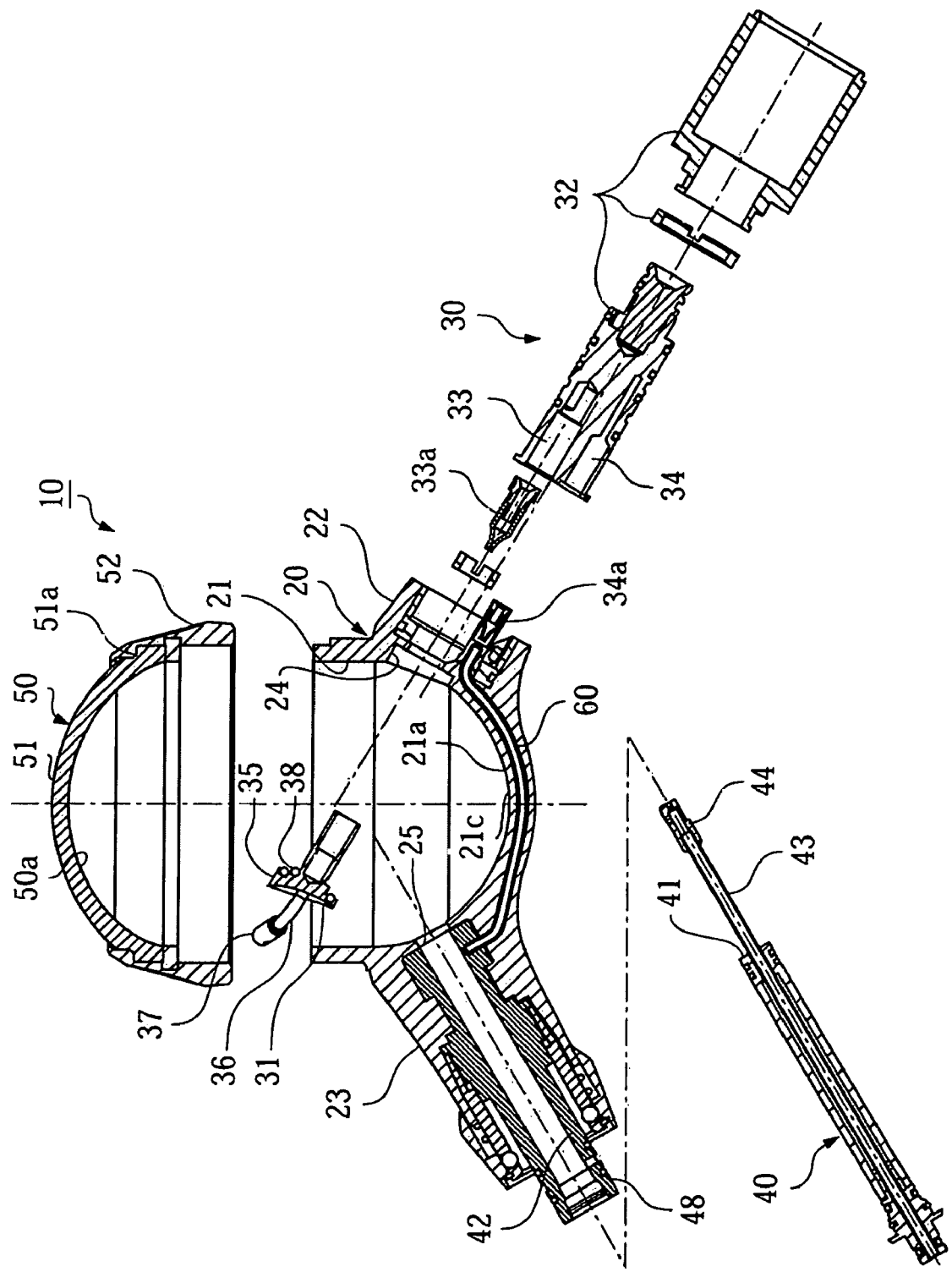
FIG. 2 is a development showing the structure of parts of the handpiece.
Figure 3:
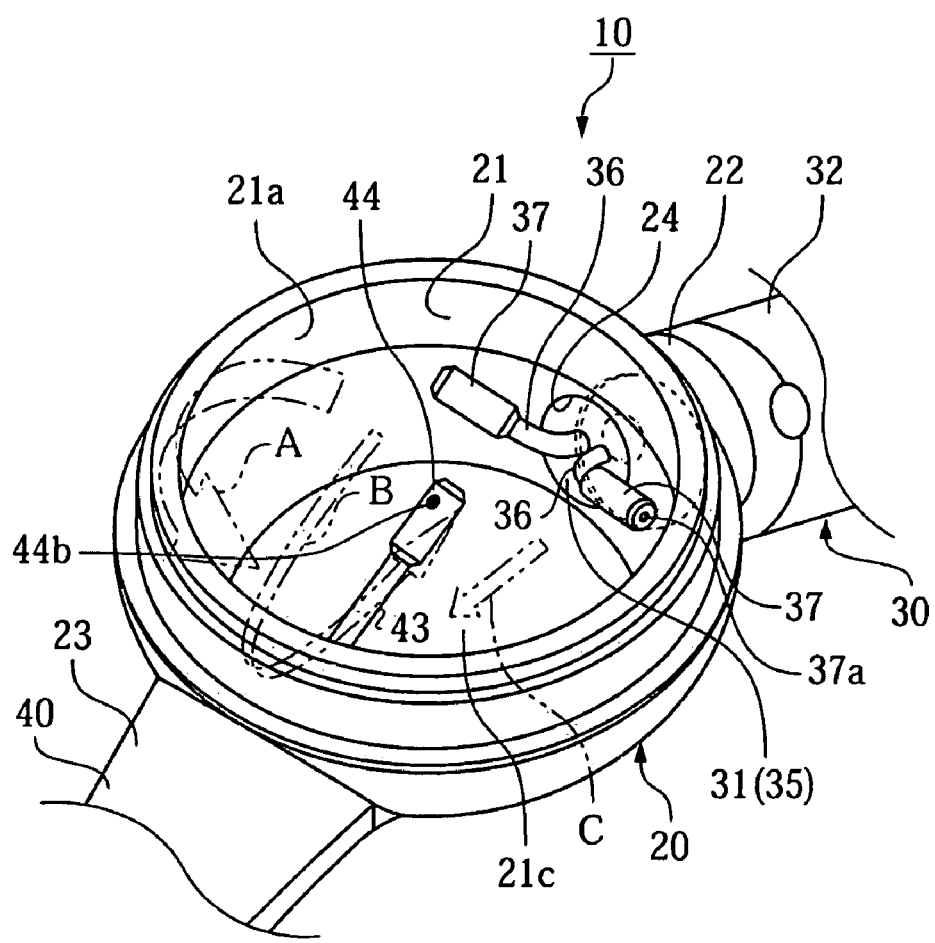
FIG. 3 is a perspective view showing main parts of the handpiece.

FIGS. 1 to 3 are diagrams to explain the structure of a tooth surface cleaning handpiece (a dental handpiece) 10 in this exemplary embodiment. FIG. 1 is a sectional view of the handpiece 10, FIG. 2 is a development of parts of the handpiece 10, and FIG. 3 is a perspective view showing main parts of the handpiece 10.

As shown in FIGS. 1 to 3, the handpiece 10 is provided with a handpiece body 20, a blowout nozzle part (an air supply path) 30, and a suction nozzle part (a mixture conveyance path) 40.

The handpiece body 20 has a concavity 21 for housing a powder of calcium carbonate, baking soda or the like used in tooth surface cleaning, a blowout nozzle holding part 22 to which the blowout nozzle part 30 is attached, and a nozzle holding part 23 to which the suction nozzle part 40 is attached.

As shown in FIGS. 1 and 2, the concavity 21 opens upward in the diagrams. In this concavity 21, a cap 50 covering the concavity 21 is detachably attached to the handpiece body 20 by means of a screw and the like. A vessel that contains a powder is formed by the concavity 21 and the cap 50, and a space S that is spherical as a whole is formed by an inner circumferential surface 21a of the concavity 21 and an inner circumferential surface 50a of the cap 50.

Two openings 24, 25 are formed in prescribed positions of the inner circumferential surface 21a of the concavity 21. A blowout nozzle body (blowout means) 31 of the blowout nozzle part 30 is disposed in one opening 24, and a suction nozzle body 41 of the suction nozzle part 40 is disposed in the other opening 25.

Furthermore, in the handpiece body 20, on the outer circumferential side of the concavity 21, i.e., on the outer side of a space S, there is formed a flow path which provides communication between the blowout nozzle part 30 and the suction nozzle part 40 and through which water is caused to flow (a water conveyance path) 60. This flow path 60 is formed, during the fabrication of the handpiece body 20 formed by molding, by setting a pipe material worked beforehand in a prescribed shape in a molding die and performing molding in this state.

The blowout nozzle part 30 is composed of the above-described blowout nozzle body 31 and a coupler part 32 for connecting a pipe from an unillustrated compressor. The blowout nozzle body 31 is attached, in the opening 24, to the handpiece body 20 from the inner circumferential surface 21a side of the concavity 21, and the coupler part 32 is attached, in the opening 24, to the handpiece body 20 from the outer side of the concavity 21. The blowout nozzle body 31 and the coupler part 32 are attached in such a manner that the handpiece body 20 is sandwiched between the blowout nozzle body 31 and the coupler part 32 in the opening 24 by means of a fitting structure using an O-ring and the like.

By use of an appropriate coupler structure, a pipe from an unillustrated compressor can be attached to and detached from the coupler part 32 by one-touch operation. By use of a double pipe structure and the like, the pipe from the compressor independently feeds compressed air blown out of the compressor and water supplied from an unillustrated water tank. In the coupler part 32 there are formed a flow path 33 of compressed air and a flow path of water (a water conveyance path) 34, and compressed air and water fed in from a connected pipe (shown in the figure) flow in. The flow paths 33, 34 are provided with check valves 33a, 34a, respectively, thereby preventing the backflow of the compressed air and water that have flown in.

The compressed air that has flown into the flow path 33 of the coupler part 32 is fed into the blowout nozzle body 31. On the other hand, the water that has flown into the flow path 34 flows into a flow path 60.

As shown in FIG. 3 and FIGS. 4(A) to 4(D), the blowout nozzle body 31 is composed of a base part 35 fixed to the opening 24, two pipes 36 in pair extending from the base part 35 to the inward side of the concavity 21, and a nozzle (a blowout nozzle) 37 provided in a tip end portion of each of the pipes 36.

The surface of the base part 35 forms a surface continuous to the inner circumferential surface 21a, with the blowout nozzle body 31 attached to the inner circumferential surface 21a of the concavity 21.

The two pipes 36 in pair have a shape symmetrical with each other and are provided so as to open to two sides from the base part 35. The pipe 36 is in communication with the flow path 33, feeds compressed air to the nozzle 37, and has also the function of maintaining the nozzle 37 in a prescribed position and direction. As a result of this, one nozzle 37 and the other nozzle 37 are provided symmetrically, with a surface containing an axis line P1 connecting the center C of the space S and the blowout nozzle part 30 and an axis line P3 of a suction pipe 43, which will be described later, sandwiched therebetween.

The nozzle 37 is supported by the pipe 36 in the vicinity of the base part 35 along the inner circumferential surface 21a of the concavity 21. Now taking concrete values as example, in each of the nozzles 37, the center axis line P2 thereof is provided so as to be inclined with respect to the axis line P1 at an angle of elevation $\theta=10°$ to the opening side of the concavity 21. In this manner, the nozzle 37 is provided so as to be substantially parallel to the part of the inner circumferential surface 21a of the concavity 21 where the nozzle 37 comes close.

As shown in FIGS. 4A to 4D, the nozzle 37 has a roughly cylindrical outer shape. A main blowout hole 37a that blows out compressed air in a direction along the center axis line of the nozzle 37 is formed in a tip end portion of the nozzle 37, and a blowout hole (a second blowout hole) 37b and a blowout hole (a third blowout hole) 37c are formed in an outer circumferential surface thereof. The blowout hole 37a is intended for generating a stream of air along the inner circumferential surface of the substantially spherical space S, which is formed by the concavity 21 and the cap 50. The air blown out of the blowout hole 37a flows along the wall surface of the space S from a side where the blowout nozzle body 31 is provided in the space S aiming at a side opposed to this side. For this reason, it is preferred that the blowout hole 37a blow out the air aiming at a part where the width of the concavity 21 becomes a maximum as viewed from the place where the blowout nozzle body 31 is provided.

Figure 4A:
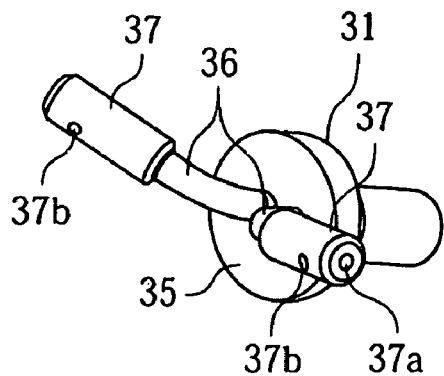
FIGS. 4A to 4D are diagrams showing a blowout nozzle body.
Figure 4B:
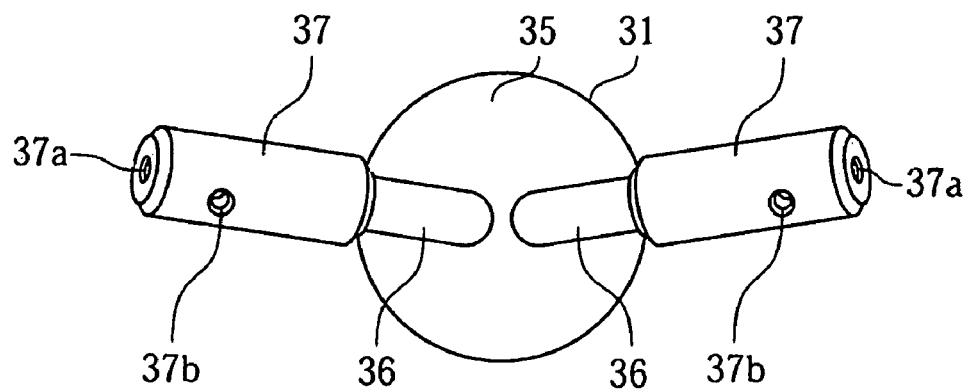
Figure 4C:
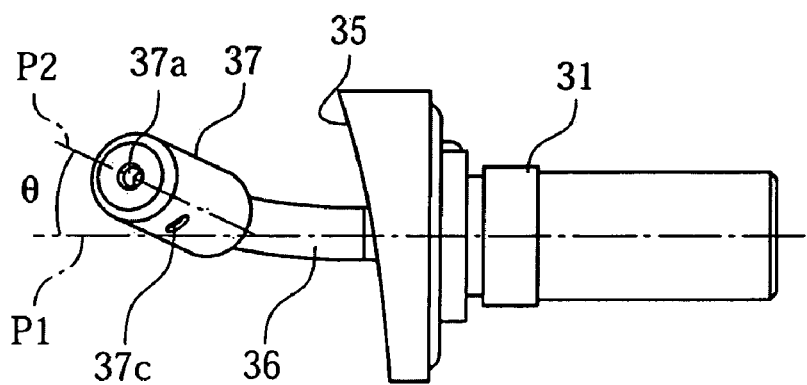
Figure 4D:
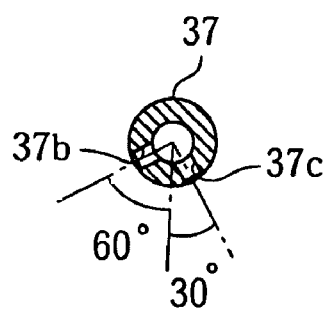

The blowout hole 37b is intended for feeding compressed air to the vicinity of the surface of a powder in the concavity 21 when the amount of the powder contained in the concavity 21 is large, thereby to stir the powder. The blowout hole 37c is intended for feeding compressed air aiming at a bottom part 21c of the concavity 21, whereby the powder is stirred by causing the powder to rise up by feeding the compressed air to the bottom part 21c in the concavity 21 when the remaining amount of the powder in the concavity 21 is small. For this reason, as shown in FIG. 4D, when the cross-section of the nozzle 37 is viewed in a plane orthogonal to the center axis line, the blowout hole 37b is inclined 60°, for example, to the center C side of the space C with respect to the vertical downward direction, and the blowout hole 37c is inclined 30°, for example, to the inner circumferential surface 21a side of the concavity 21 with respect to the vertical downward direction.

The compressed air blown out of this nozzle 37 causes the powder in the concavity 21 to rise up within the space S, thereby to stir the powder, with the result that the powder and the air are brought into a mixed condition.

Because in this blowout nozzle body 31, the installation angle of the nozzle 37 in the concavity 21 is important, it is preferred that the installation angle to the handpiece body 20 be capable of easily positioned by use of positioning means using a ball 38 and the like. When the ball 38 is used, the installation angle of the blowout nozzle body 31 can be positioned by urging the ball 38 by use of a spring and the like, and by housing this ball 38 in a groove or a concavity formed on the handpiece body 20 side.

In the suction nozzle part 40, the suction nozzle body 41 is supported on the handpiece body 20 by means of a cylindrical holder 42 provided in the handpiece body 20. The suction nozzle body 41 and the holder 42 are constructed in such a manner that by use of an O-ring and the like, the suction nozzle body 41 can be inserted and extracted in the axis line direction thereof.

A suction pipe 43 is provided on the center axis line of the suction nozzle body 41. The suction pipe 43 protrudes from the inner circumferential surface 21a of the concavity 21 toward the center C of the space S, and a nozzle 44 is provided in a tip end portion thereof. The nozzle 44 is intended for sucking in a mixture of the powder and the air within the space S, and for example, on a tip end surface thereof and on the upward side of an outer circumferential surface thereof, a suction hole 44a and a suction hole 44b, respectively, are provided. The mixture of air and powder within the space S sucked in from the suction holes 44a, 44b in the suction nozzle 44 flows through the suction pipe 43 and is fed to a jet nozzle 70 attached to a tip end of the handpiece body 20.

As shown in FIG. 1, the suction nozzle body 41 is roughly D-shaped as viewed in cross-section and part of the outer circumferential surface is flat. In contrast, the holder 42 that holds the suction nozzle body 41 is roughly circular as viewed in section. As a result of this, between the inner circumferential surface of the holder 42 and the outer circumferential surface of the suction nozzle body 41, there is formed a space 45 that is continuous in the direction in which the axis line of the suction nozzle body 41 extends. An end portion of the above-described flow path 60 is held by the holder 42, and one end 45a of the space 45 is in communication with the flow path 60. The other end 45b of the space 45 is open to the tip of the holder 42. As a result of this, the space 45 forms a flow path of water (a water conveyance path) 46 continuous to the flow path 60. In this manner, by devising the cross-sectional shape of the suction nozzle body 41, it is possible to form the flow path of water 46 without the installation of a separate dedicated pipe and the like, and it is possible to simplify the construction and to facilitate manufacturing.

Part of the holder 42 protrudes from the handpiece body 20, and this part provides a coupler part 48 for attaching the jet nozzle 70 to a tip end portion of the handpiece body 20. The coupler part 48 can attach the jet nozzle 70 in a detachable condition due to the use of an appropriate coupler structure. The jet nozzle 70 is independently provided with a powder/air flow path 71 that feeds a mixture of powder and air fed in from the suction pipe 43 and a water flow path 72 that feeds water fed in by the flow path 46. The mixture of powder and air fed by the powder/air flow path 71 and the water fed by the water flow path 72 are mixed in a tip end portion of the jet nozzle 70 and blown to outside.

This handpiece 10 is used by connecting piping that feeds compressed air and water from a compressor and a water tank, which are not shown, to the coupler part 32 of the blowout nozzle part 30 and connecting the jet nozzle 70 to the coupler part 48 of the suction nozzle part 40. And when the handpiece 10 is used, that is, when tooth surface cleaning is performed, powder is charged to a prescribed level within the concavity 21.

After that, by operating an unillustrated foot switch and the like, compressed air is fed from the compressor and water is fed from the water tank. The flow rates of the compressed air and water at this time are kept in a given pressure range by use of a regulator and the like, and the amounts of the jetted compressed air and water can be adjusted by operating the foot switch and the like.

The compressed air fed from the compressor flows through the two pipes 36 of the blowout nozzle body 31 from an unillustrated pipe connected to the coupler part 32 and is blown out of the nozzle 37 into the space S.

At this time, the compressed air blown out of the blowout hole 37a formed in the tip end portion of the nozzle 37 into the space S generates, within the space S, a stream of air (arrow A in FIG. 3) along the inner circumferential surface of the space S. As a result of this, within the space S, the powder contained in the concavity 21 is caused to rise up and becomes mixed with the air within the space S.

Furthermore, when the amount of the powder contained in the concavity 21 is large and the blowout hole 37b is completely buried in the powder, the air from the blowout hole 37b changes the condition of the powder and the powder begins to float and fly in all directions. When the top surface level of the powder that has accumulated is below the blowout hole 37b, the air is blown out aiming at the vicinity of the surface of the powder that has accumulated in the concavity 21 and a stream of this air (arrow B in FIG. 3) causes the powder to rise up, making it possible to improve the mixed condition of the powder and the air within the space S.

On the other hand, when the remaining amount of the powder in the concavity 21 is small, a stream of the compressed air blown out of the blowout hole 37c (arrow C in FIG. 3) can cause the powder to rise up from a bottom part 21c in the concavity 21 and also in this condition, it is possible to improve the mixed condition of the powder and the air within the space S. As a result of this, it is also possible to prevent the powder from remaining in the bottom part 21c of the concavity 21.

Within the space S, the powder and the air that have come to a mixed condition are sucked in from the suction holes 44a, 44b of the nozzle 44, flow through the suction pipe 43, and are conveyed to the powder/air flow path 71 of the jet nozzle 70 attached to the tip end portion of the handpiece body 20. At this time, even when the amount of the powder contained in the concavity 21 is large, due to the presence of the suction hole 44b formed on the top surface side of the nozzle 44, it is possible to prevent the nozzle 44 from being buried in the powder that has accumulated in the concavity 21 and to reliably suck in the mixture of powder and air.

On the other hand, the water fed from the water tank flows through the flow path 34 of the blowout nozzle part 30, the flow path 60 in the handpiece body 20 and the flow path 46 of the suction nozzle part 40, and is fed to the flow path 72 of the jet nozzle 70.

And in the tip end portion of the jet nozzle 70, the mixture of powder and air jetted from the end portion of the powder/air flow path 71 and the water jetted from the water flow path 72 are mixed together to become a mixture of these, which is blown out to the outside. The mixture of powder, air and water is blown on the surfaces of tooth, whereby the surfaces of tooth are cleaned.

Incidentally, as described above, compressed air is used in the handpiece 10. It is preferred that the cap 50 provided so as to cover the opening of the concavity 21 be of the explosion-proof construction, so that the pressure of the compressed air in the handpiece 10 does not become excessively high, for example, when a trouble occurs in the regulator of the compressor that feed compressed air into the handpiece 10.

For this reason, in this exemplary embodiment, the cap 50 is composed of a cap body 51 made of resin, and a cap holding member 52 having a screw groove for attaching this cap body 51 to the handpiece body 20. And the cap 50 is attached to the handpiece body 20, with an outer circumferential portion of the cap body 51 held with the cap holding member 52. In this connection, in the outer circumferential portion of the cap body 51, there is formed a stepped portion 51a, and as a result of this, in the part of the stepped portion 51a, the wall thickness of the cap body 51 is smaller than other portions. This stepped portion 51a is used also to fix the cap body 51 by use of the cap holding member 52.

By ensuring that as described above, in the part of the stepped portion 51a, the wall thickness of the cap body 51 is smaller than other portions, when the pressure of the compressed air in the handpiece 10 has become excessively high, the cap body 51 becomes broken in the part of the stepped portion 51a, thereby making it possible to release the pressure.

According to the handpiece 10 described above, in the two nozzles 37 in pair that blow out compressed air into the space S where the powder and the air are mixed, the compressed air that has been blown out of the blowout hole 37a formed in the tip end portion of the nozzle 37 into the space S generates a stream of air from the side where the nozzle 37 is provided in the space S aiming at the opposite side along the inner circumferential surface of the space S, with the result that within the space S, the powder contained in the concavity 21 is caused to rise up and becomes mixed with the air within the space S. Furthermore, when the amount of the powder contained in the concavity 21 becomes large, the blowout hole 37b formed in the outer circumferential surface of the nozzle 37 causes the powder in the vicinity of the surface of the powder that has accumulated in the concavity 21 to rise up, thereby making it possible to improve the mixed condition of the powder and the air in the space S. On the other hand, when the remaining amount of the powder in the concavity 21 becomes small, the compressed air that has been blown out of the blowout hole 37c formed in the outer circumferential surface of the nozzle 37 can cause the powder to rise up from the bottom part 21c in the concavity 21. Also in this condition, it is possible to improve the mixed condition of the powder and the air within the space S. As a result of this, it is also possible to prevent the powder from remaining in the bottom part 21c of the concavity 21.

As described above, the mixed condition of the powder and the air in the space S is improved, and besides, the mixing of the powder and the air can be promoted when the amount of powder is large as well as the amount of powder is small. Therefore, it is possible to stabilize the flow rate of a blown-out powder while raising the cutting efficiency and to cause the stock of the filled powder to last longer.

Embodiment

The effect of the above-described constituent features was ascertained. The results are described below.

Example 1

In a handpiece 10 as described above, the diameter of a space S was 36 mm, and the diameter of blowout holes 37a, 37b, 37c of a nozzle 37 was each 0.5 mm. The blowout hole 37b was formed so as to be inclined 60°, for example, to the center C side of the space S with respect to the vertical downward direction, and the blowout hole 37c was formed so as to be inclined 30°, for example, to the inner circumferential surface 21a side of a concavity 21 with respect to the vertical downward direction. And 15 g of calcium carbonate were contained in the concavity 21 as a powder, and compressed air at a pressure of 0.3 MPa was fed in.

The relationship between elapsed time and cumulative cut area was found from the remaining amount of the powder each time one minute lapsed.

Example 2

Figure 5:
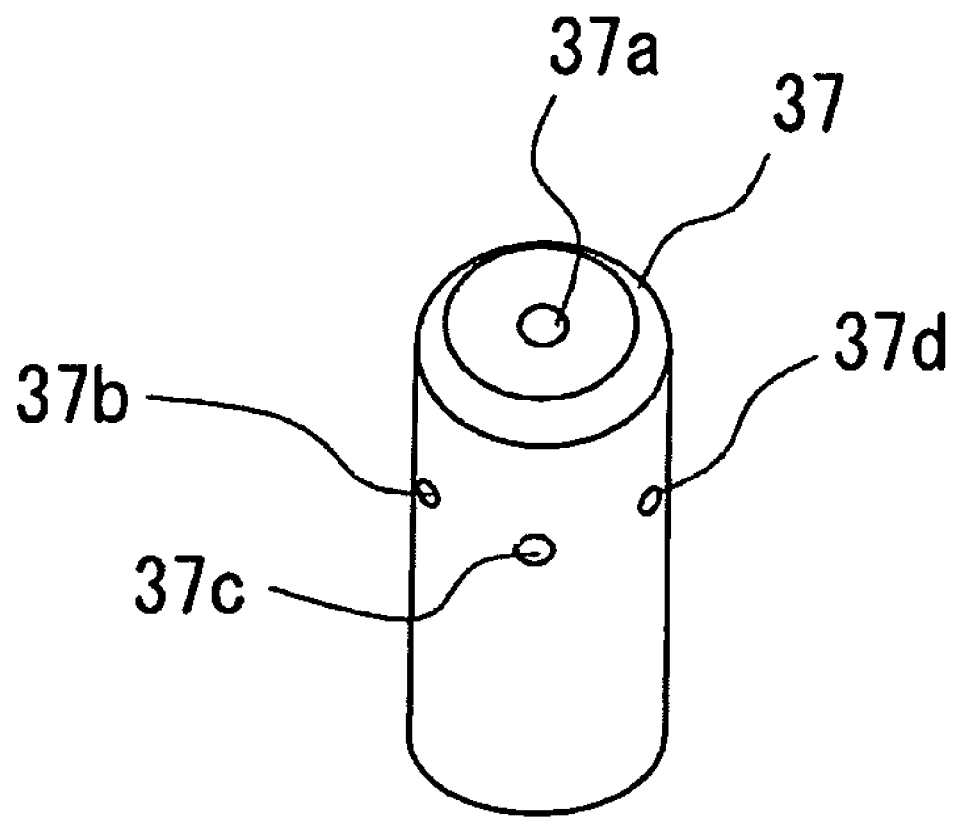
FIG. 5 is a diagram showing the structure of a nozzle used in Example 2.

For comparison, as shown in FIG. 5, a blowout hole 37a formed in a tip end portion of a nozzle 37 had a diameter of 0.4 mm, and three blowout holes 37b, 37c, 37d having a diameter of 0.4 mm were formed in the outer circumferential surface to have an angle of 60° each. By using this nozzle 37, the relationship between elapsed time and cumulative cut area was found in the same way as described above.

Example 3

Two blowout holes having a diameter of 0.5 mm were formed only in an outer circumferential surface of the nozzle 37 without forming a blowout hole at the tip end thereof. One of the blowout holes formed in the outer circumferential surface is intended for blowing out air obliquely to ensure that the air flows from the side where the nozzle 37 is provided aiming at the opposite side thereof along an inner circumferential surface 12a of a concavity 21. By using this nozzle 37, the relationship between elapsed time and cumulative cut area was found in the same way as described above.

Comparative Example 1

By using a conventional product proposed by the applicant of the present invention (a product to which the technique of Japanese Patent No. 3299736 is applied), the relationship between elapsed time and cumulative cut area was found in the same way as described above. The diameter of the space S was 40.5 mm, a pair of nozzles was arranged in the diametrical direction of the space S, and each nozzle was caused to blow out compressed air aiming at a wall surface of the space S. Within the space S, 15 g of calcium carbonate as a powder were contained and the pressure of the compressed air was 0.3 MPa.

Figure 6:
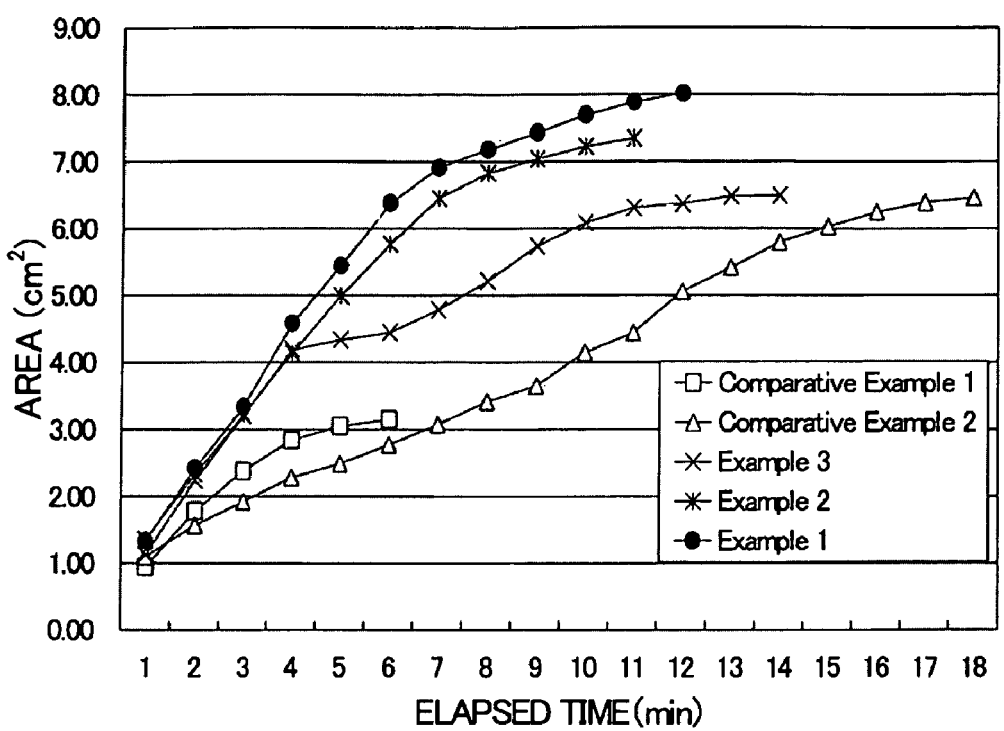
FIG. 6 is a diagram showing results of the present examples.

The relationship between elapsed time and cumulative cut area in Examples 1, 2, 3 and Comparative Example 1 is shown in FIG. 6.

In Comparative Example 1 of the conventional product, the powder ceased to be blown out in 6 minutes, whereas in Examples 1 to 3, the powder continued to be blown out for more than 11 minutes. As a result of this, as in the present invention, by arranging the nozzle 37 along the inner wall surface of the space S and by ensuring that the air flows from the side where the nozzle 37 is provided aiming at the opposite side along the inner circumferential surface 21a of the concavity 21, it was ascertained that the flow rate of a blown-out powder becomes stable and that the stock of the powder is caused to last longer.

From a comparison between Examples 1 and 2 in which the blowout hole 37a is formed in the tip end portion and Example 3 in which the blowout hole 37a is not formed in the tip end portion, it became apparent that by forming the blowout hole 37a in the tip end portion, the cumulative cut area is large at any elapsed time, resulting in a higher cutting efficiency. That is, it might be thought that by blowing the air from the blowout hole 37a in the tip end portion aiming at a part where the width of the space S becomes a maximum as viewed from the nozzle 37 to cause the air to flow along the outer circumferential surface of the space S, a swirl is generated within the space S and the mixed condition of the powder and the air is improved, resulting in a higher cutting efficiency.

From a comparison between Example 1 and Example 2 in which the arrangement of the blowout hole formed in the outer circumferential surface is different, it was ascertained that the cutting efficiency is more raised by the arrangement of the blowholes 37a, 37b concretely shown in the above-described exemplary embodiment. In Example 1, the cutting efficiency is higher than in Example 2 and also the stock of the powder is caused to last longer although the hole diameter is made larger than in Example 2. This is because cutting is performed with good efficiency.

Comparative Example 2

Figure 7:
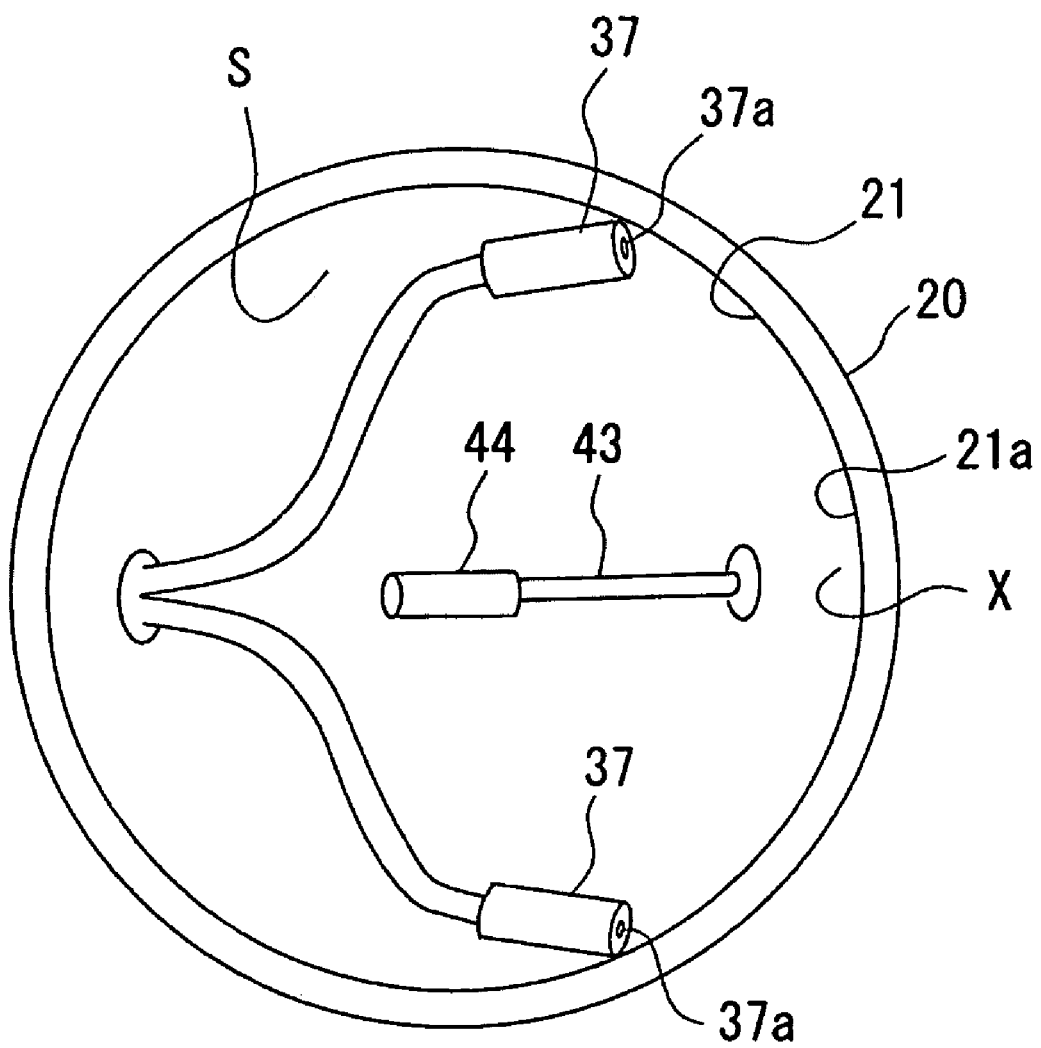
FIG. 7 is a diagram showing the arrangement of a nozzle in Comparative Example 2.

Also in a case where the nozzle 37 used in Example 1 was arranged as shown in FIG. 7, the relationship between elapsed time and cumulative cut area was found in the same way as in Example 1. The results are shown in FIG. 6.

As shown in FIG. 6, it is apparent that even with the same nozzle 37 as used in Example 1 above, the cutting efficiency is not improved if the air blown out of a pair of nozzles 37 is blown so as to be concentrated on one point X on the inner circumferential surface of the space S on the edge of the wall of the space S. From this it is apparent that it is preferred that the nozzle 37 is arranged so as to blow out the air from the side where the nozzle 37 is provided aiming at the opposite side along the inner circumferential surface of the space S, with the result that the nozzle 37 can generate a swirl with good efficiency within the space S.

Figure 8:
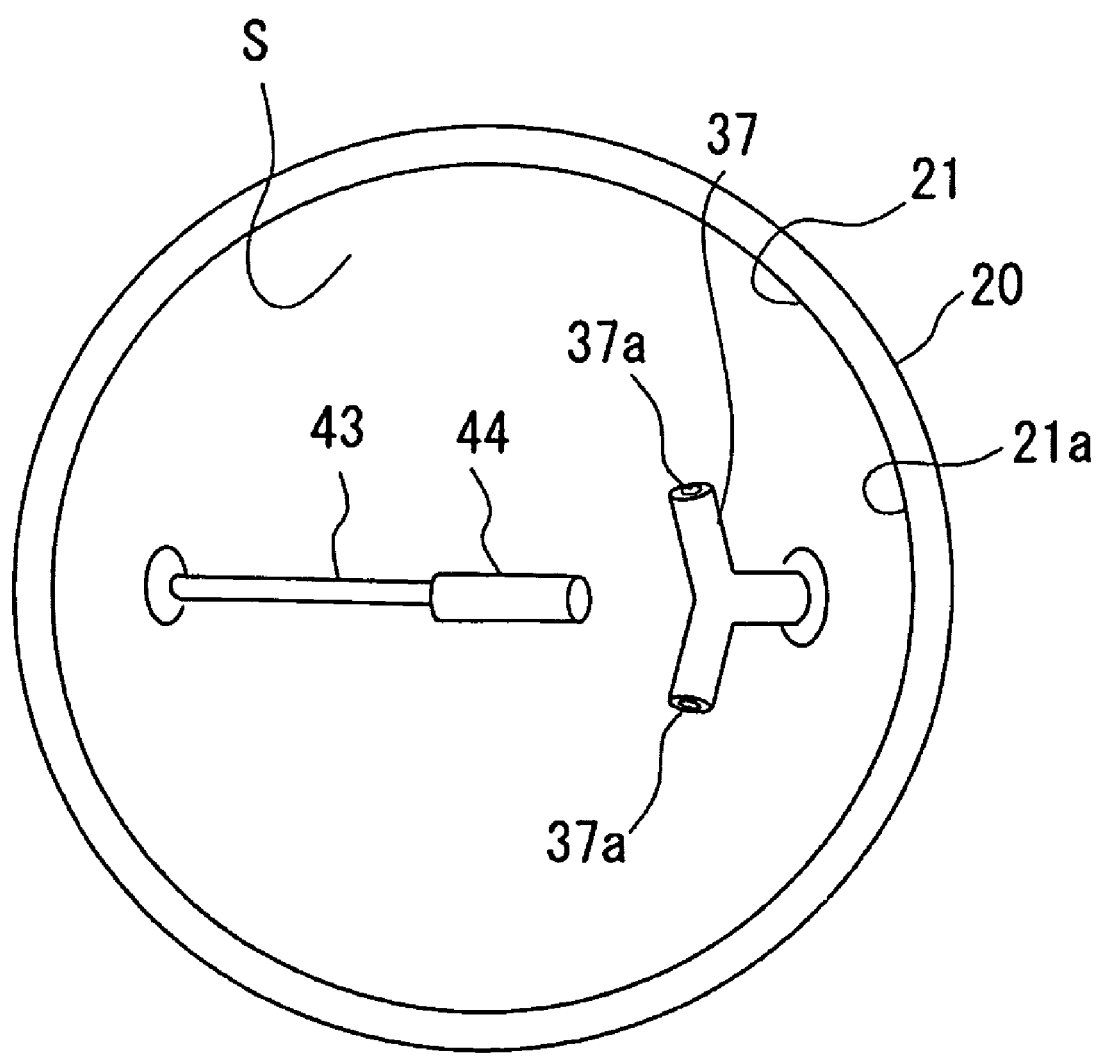
FIG. 8 is a diagram showing another example of a blowout nozzle body.

In the above-described exemplary embodiment, the blowout nozzle body 31 is composed of the two pipes in pair 36 and the nozzle 37 provided in the tip end portion of each of the pipes 36. However, the blowout nozzle body 31 may have any construction so long as the blowout nozzle body 31 can blow out air from the two blowout holes in pair 37a in a direction as shown in the above-described exemplary embodiment. For example, as shown in FIG. 8, the blowout nozzle body 31 may be roughly T-shaped as one piece so that two blowout holes in pair 37a are provided in two end portions of the T. The blowout nozzle body 31 may also have other shapes.

The construction of each part of the handpiece 10 was described. The constructions described in the above-described exemplary embodiment can be appropriately selected and it is possible to make appropriate changes to other constructions without departing the spirit of the present invention.

What is claimed is:

1. A dental handpiece used to perform dental care by blowing a mixture of air and a powder on teeth along with water from a jet nozzle, comprising:
    a vessel having a spherical space that contains the powder therein;
    an air supply path that supplies the air to be mixed with the powder to the space;
    a mixture conveyance path for conveying the mixture of the powder and the air to the jet nozzle, wherein the mixture is roughly inputted from a middle part of the space; and a water conveyance path for conveying water to be blown on teeth along with the mixture to the jet nozzle;

wherein the air supply path is provided with blowout means that blows out the air into the space within the vessel in a vicinity of a wall surface of the vessel, the blowout means comprises two pipes in pair having a shape symmetrical with each other, each of the two pipes comprises a respective nozzle provided in a tip end portion, the respective nozzle has a roughly cylindrical outer shape and having, within the vessel, a main blowout hole that blows out the air from a side where the blowout means is provided aiming at an opposite side thereof along the wall surface of the vessel, the main blowout hole blows out compressed air in a direction along a center axis of the respective nozzle and is formed in a tip end portion of the respective nozzle, and the respective nozzle comes close to a part of an inner circumferential surface and is provided so as to be substantially parallel to the part of the inner circumferential surface, further wherein in addition to the main blowout hole, the respective nozzle includes at least two blowout holes oriented at specific inclinations, the at least two blowout holes being formed in an outer circumferential surface of the respective nozzle.

2. The dental handpiece according to claim 1, wherein the main blowout hole is formed so as to blow out the air aiming at a part where the width of the space becomes a maximum as viewed from the blowout means along an outer circumferential surface of the space.

3. The dental handpiece according to claim 1, wherein one of the at least two blowout holes blows out the air aiming at a vicinity of a top surface level of the powder within the space.

4. The dental handpiece according to claim 1, wherein one of the at least two blowout holes blows out the air aiming at a bottom part of a concavity, wherein the vessel is formed by the concavity and a cap.

5. The dental handpiece according to claim 1, wherein the blowout means is provided with positioning means for positioning the blowout means at a mounting angle to the vessel.

6. The dental handpiece according to claim 1, wherein the water conveyance path is formed by burying a pipe in an interior of the vessel or by providing a pipe along an outer surface of the vessel.

* * * * *